United States Patent [19]

Hay et al.

[11] Patent Number: 4,943,312
[45] Date of Patent: Jul. 24, 1990

[54] HERBICIDAL THIAZOLE DERIVATIVES

[75] Inventors: James V. Hay, Newark, Del.; Anthony D. Wolf, Elkton, Md.

[73] Assignee: E. I. Du Pont de Nemours and Company, Wilmington, Del.

[21] Appl. No.: 609,695

[22] Filed: May 14, 1984

Related U.S. Application Data

[63] Continuation-in-part of Ser. No. 479,363, Apr. 4, 1983, abandoned.

[51] Int. Cl.$^5$ .................... C07D 417/12; A01N 47/36
[52] U.S. Cl. ......................................... 71/90; 544/320; 544/331

[58] Field of Search ....................... 544/320, 331, 332; 71/90

[56] References Cited

U.S. PATENT DOCUMENTS 4,441,910  4/1984  Shapiro ................................. 71/90

Primary Examiner—Robert Gerstl

[57] ABSTRACT

Certain N-[(heterocyclic)aminocarbonyl]thiazolesulfonamides, such as N-[(4-methoxy-6-methylpyrimidin-2-yl)aminocarbonyl]-4-thiazolesulfonamide, are useful as herbicides and/or plant growth regulants.

12 Claims, No Drawings

HERBICIDAL THIAZOLE DERIVATIVES

BACKGROUND OF THE INVENTION

This invention relates to novel N-[(heterocyclic-)aminocarbonyl]thiazolesulfonamides where the heterocycle is pyrimidine or triazine, to herbicidal compositions containing them and to methods of using them to control the growth of undesired vegetation.

New compounds effective for controlling the growth of undesired vegetation are in constant demand. In the most common situation, such compounds are sought to selectively control the growth of weeds in useful crops such as cotton, rice, corn, wheat and soybeans, to name a few. Unchecked week growth in such crops can cause significant losses, reducing profit to the farmer and increasing costs to the consumer. In other situations, herbicides are desired which will control all plant growth. Examples of areas in which complete control of all vegetation is desired are areas around fuel storage tanks, ammunition depots and industrial storage areas. There are many products commercially available for these purposes, but the search continues for products which are more effective, less costly and environmentally safe.

A numer of different types of N-[(heterocyclic-)aminocarbonyl]arylsulfonamides are known as herbicides. Two of the first patents to issue on such compounds are U.S. Pat. Nos. 4,169,719 and 4,127,405, issued on Oct. 2, 1979 and Nov. 28, 1978, respectively. These patents disclose compounds of the general formula

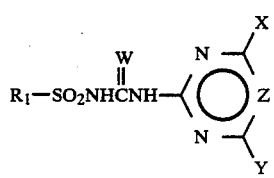

where
W can be O or S,
Z can be N or CH, and
R is optionally substituted benzene, optionally substituted thiophen, optionally substituted furan or naphthalene.

Later publications have disclosed similar compounds where $R_1$ is a thiophene or pyrrole. See, for example, European Patent Applications 81302461.9, published Dec. 9, 1981, 82301500.3, published Nov. 17, 1982, 80304287.8, published Jun. 10, 1981, and 81301874.4, published Nov. 4, 1981. Nowhere in the art is there a disclosure of N-[(heterocyclic)-aminocarbonyl]-thiazolesulfonamides or any indication that such novel compounds would be useful as herbicides.

SUMMARY OF THE INVENTION

It has now been found that the novel compounds of Formula I possess herbicidal and/or plant growth regulant utility.

$$QSO_2NHCONHA \qquad I$$

where Q is

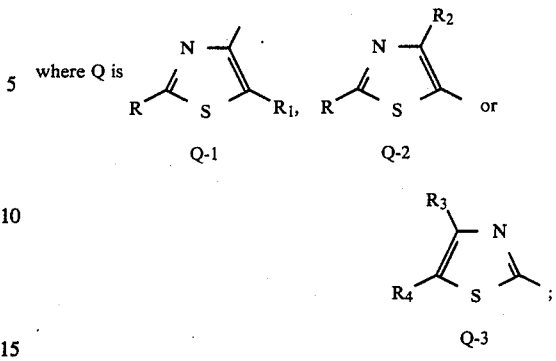

R is H, $C_1$–$C_3$ alkyl or $CH_3C(O)NH$;
$R_1$ is H, $C_1$–$C_3$ alkyl, $C_1$–$C_3$ alkoxy, $C_1$–$C_3$ alkylthio, or $C_1$–$C_3$ alkoxycarbonyl;
$R_2$ is H, $C_1$–$C_3$ alkyl, $C_1$–$C_3$ alkoxy, $C_1$–$C_3$ alkylthio, $C_1$–$C_3$ alkoxycarbonyl, $NO_2$, Cl, Br or $CF_3$;
$R_3$ is H, Cl or $CH_3$;
$R_4$ is H, Cl or $CH_3$;
A is

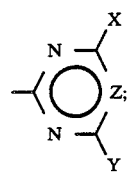

X is $CH_3$, $C_2H_5$, $OCH_3$, $OCF_2H$, $OC_2H_5$ or $CH_2OCH_3$;
Y is $CH_3$, $OCH_3$, $OCF_2H$ or cyclopropyl; and
Z is CH or N;
provided that (i) $R_3$ and $R_4$ are not simultaneously Cl, and (ii) when either X or Y is $OCF_2H$, then Z is CH; and argiculturally suitable salts thereof.

This invention therefore relates to novel compounds of Formula I, to herbicidal compositions containing them, and to methods of using them to control the growth of undesired vegetation.

Preferred for reasons of their high herbicidal activity, plant growth regulant activity and/or favorable ease of synthesis are the following groups of compounds:

(1) Compounds of Formula I where Z is CH.
(2) Compounds of Formula I where Z is CH and, when Q is Q-3, then $R_4$ is H.
(3) Compounds of Formula I where Z is CH and Q is Q-1 or Q-2.
(4) Compounds of Formula I where Z is CH and Q is Q-1, R is H or $CH_3$, and $R_1$ is H, $CH_3$, $C_1$–$C_2$ alkoxy or $C_1$–$C_2$ alkoxycarbonyl.

The following compounds are specifically preferred for reasons of their high herbicidal activity, plant growth regulant activity and/or favorable ease of synthesis:

N-[(4-methoxy-6-methylpyrimidin-2-yl)aminocarbonyl]-4-thiazolesulfonamide, m.p. 196°–200°(d);
N-[(4,6-dimethoxypyrimidin-2-yl)aminocarbonyl]-4-thiazolesulfonamide, m.p. 201°–203° C.; and
5-ethoxy-N-[(4,6-dimethoxypyrimidin-2-yl)aminocarbonyl]-2-methyl-4-thiazolesulfonamide.

DETAILED DESCRIPTION

Synthesis

The compounds of this invention where Q and A are as previously defined but R is other than $CH_3CONH$, may be prepared, as shown in Equation 1, by reaction of an appropriately substituted sulfonyl isocyanate of Formula II with the appropriate heterocyclic amine of Formula III.

Equation 1

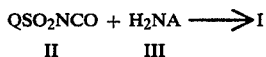

$$QSO_2NCO + H_2NA \longrightarrow I$$
$$\text{II} \qquad \text{III}$$

The reaction of Equation 1 is generally carried out by adding a solution of the sulfonyl isocyanate II in an inert solvent, such as methylene chloride or acetonitrile, to a solution or suspension of the heterocyclic amine III in the same solvent. The mixture is stirred from about one to twenty-four hours at temperatures from ambient to the reflux temperature of the solvent. In some cases, the reaction is exothermic and the compounds of Formula I crystallize from the reaction mixture. When the compounds of Formula I are soluble in the reaction medium, they can be isolated by evaporation of the solvent and trituration with a suitable solvent such as 1-chlorobutane or hexane.

Sulfonyl isocyanates of Formula II, where Q is as previously defined and R is other than $CH_3CONH$, can be prepared, as shown in Equation 2, by reaction of sulfonamides of Formula IV with phosgene in the presence of an alkyl isocyanate, such as butyl isocyanate, in an inert solvent, such as xylene or chlorobenzene, according to the procedure of H. Ulrich and A. A. Y. Sayigh, "New Methods of Preparative Organic Chemistry", Vol. VI. p. 223–241, Academic Press, New York and London, W. Foerst. Ed.

Equation 2

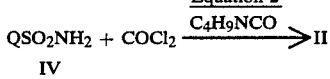

$$QSO_2NH_2 + COCl_2 \xrightarrow{C_4H_9NCO} II$$
$$\text{IV}$$

Alternatively, the reaction shown in Equation 2 can be carried out in the presence of a catalytic amount of a tertiary amine, such as triethylamine or diaza[2.2.2-]bicyclooctane, by the procedure described in European Patent Application No. 80301848.0, published Jan. 7, 1981.

Alternatively, many compounds of Formula I, where Q and A are as previously defined, but $R_1$ and $R_2$ are other than $C_1$-$C_3$ alkoxycarbonyl, may be prepared by the method described in Equation 3, namely, by reaction of a sulfonamide of Formula IV, where Q is as previously defined but $R_1$ and $R_2$ are other than $C_1$-$C_3$ alkoxycarbonyl, with a heterocyclic carbamate of Formula V in the presence of at least one molar equivalent of trimethylaluminum.

Equation 3

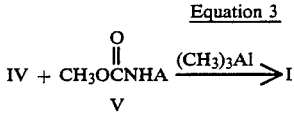

$$IV + CH_3O\overset{O}{\underset{\|}{C}}NHA \xrightarrow{(CH_3)_3Al} I$$
$$\text{V}$$

The reaction of Equation 4 is generally carried out in an inert solvent, such as methylene chloride or toluene, under an inert atmosphere, at temperatures from ambient up to the reflux temperature of the solvent for about 6–96 hours. The product can be isolated by addition of dilute hydrochloric acid to the cooled reaction mixture followed by separation of the organic phase, drying of the solution and evaporation of the solvent. The product can be purified by trituration wtih, or crystallization from, solvents such as 1-chlorobutane, hexane, ethanol or similar solvents.

Another procedure for the preparation of many compounds of this invention is by the reaction of a carbamate of Formula VI, where Q is as previously defined, with a heterocyclic amine III by methods analogous to the procedure described in European Patent Application 81810281.6 (Publication Number 44,807), published Jul. 3, 1981, as shown in Equation 4.

Equation 4

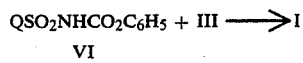

$$QSO_2NHCO_2C_6H_5 + III \longrightarrow I$$
$$\text{VI}$$

The compounds of Formula I of this invention also can be prepared, as shown in Equation 5, by contacting a sulfonamide of Formula IV, where Q is as previously defined, with a phenylcarbamate of Formula VII, where A is as previously defined, in the presence of a molecular equivalent of 1,5-diazabicyclo[5.4.0]undec-5-ene (DBU). The reaction of Equation 5 is generally carried out in an inert, water-miscible solvent, such as acetonitrile, dioxane or tetrahydrofuran, about ambient temperature for about 0.5–6 hours. The product can be isolated by dilution of the reaction medium with water, acidification, followed by purification by methods similar to those previously discussed. The carbamates of Formula VII may be prepared by the methods, or modifications thereof known to those skilled in the art, described in South African Patent Application 825,045, filed Jul. 15, 1982.

Equation 5

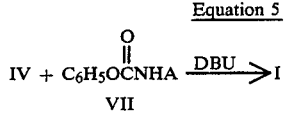

$$IV + C_6H_5O\overset{O}{\underset{\|}{C}}NHA \xrightarrow{DBU} I$$
$$\text{VII}$$

Sulfonamides of Formula IV can be prepared by amination of the corresponding sulfonyl chlorides of Formula VIII by methods well known in the art. The intermediate sulfonyl chlorides of Formula VIII can be prepared by one of the methods shown in Equation 6.

Equation 1

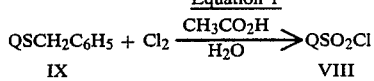

$$QSCH_2C_6H_5 + Cl_2 \xrightarrow{\frac{CH_3CO_2H}{H_2O}} QSO_2Cl \qquad A.$$
$$\text{IX} \qquad\qquad\qquad \text{VIII}$$

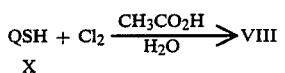

$$QSH + Cl_2 \xrightarrow{\frac{CH_3CO_2H}{H_2O}} VIII \qquad B.$$
$$\text{X}$$

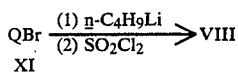

$$QBr \xrightarrow[\text{(2) } SO_2Cl_2]{\text{(1) } \underline{n}\text{-}C_4H_9Li} VIII \qquad C.$$
$$\text{XI}$$

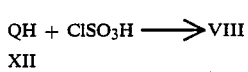

$$QH + ClSO_3H \longrightarrow VIII \qquad D.$$
$$\text{XII}$$

-continued

Equation 1

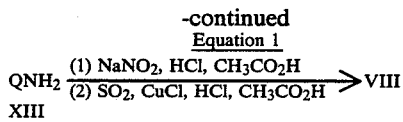

In Equations 6A and 6B, a solution or a suspension of a benzyl sulfide of Formula IX or a thiol of Formula X in aqueous acetic acid is treated wtih at least three molar equivalents of chlorine at temperatures of about 0° to 15°. The sulfonyl chloride of Formula VIII can be isolated by dilution of the reaction mixture with water, followed by either filtration or extraction with an organic solvent such as ether, methylene chloride or 1-chlorobutane.

In Equation 6C, a bromide of Formula XI is treated with one molar equivalent of n-butyl lithium, in solvents such as ether, tetrahydrofuran or dimethoxyethane, at temperatures of about −78° to −20°. The intermediate lithioheterocycle is added to an excess of sulfuryl chloride in a solvent such as hexane or ether at temperatures of about −20° to 0°. The sulfonyl chloride of Formula VIII can be isolated by addition of water to the reaction mixture, separation of the organic solution, and evaporation of the solvents.

In Equation 6D, a heterocycle of Formula XII is treated with an excess of chorosulfonic acid at temperatures of about ambient to the boiling point of chlorosulfonic for periods of from several hours to several days. The sulfonyl chlorides of Formula VIII can be isolated by pouring the reaction mixture into ice water, and either filtering the product or extracting it into an organic solvent.

In Equation 6E, a heterocyclic amine of Formula XIII is diazotized with sodium nitrite in a mixture of water, concentrated hydrochloric acid and acetic acid at temperatures from about −5° to 10°. The resulting diazonium salt is added to a mixture of sulfur dioxide, cuprous or cupric chloride, concentrated hydrochloric acid and acetic acid, and the reaction mixture is stirred at temperatures from about 0° to ambient. The solfonyl chloride of Formula VIII can be isolated by diluting the reaction mixture with water and either filtration or extraction with an organic solvent.

The synthesis of the heterocyclic amines of Formula III has been reviewed in "The Chemistry of Heterocyclic Compounds", a series published by interscience Publishers. 2-Aminopyrimidines are described by D. J. Brown in "The Pyrimidines" in Vol. XVI of the series; 2-aminotriazines are described by E. M. Smolin and L. Rapoport in "s-Triazines and Derivatives", in Vol. XIII of the series, both of the teachings of which are herein incorporated by refernce. Compounds of Formula III where X or Y is $OCF_2H$ can be prepared by the methods described in Sough African Patent Apploication 825,045.

Compounds of Formula III where Y is cyclopropyl can be prepared by the methods described in South African Patent Application 837,434.

Agriculturally suitable salts of compounds of Formula I are also useful herbicides and can be prepared in a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I (e.g., an alkali metal or quaternary amine salt) through a column packed with a cation exchange resin containing the cation to be exchanged. In this method, the cation of the resin is exchanged for that of the original salt and the desired product is eluted from the column. This method is particularly useful when the desired salt is water-soluble, e.g., a potassium, sodium or calcium salt.

Acid addition salts, useful in this invention, can be obtained by reacting a compound of Formula I or II with a suitable acid, e.g., p-toluenesulfonic acid, trichloroacetic acid or the like.

The compounds of this invention are further illustrated by the following examples, wherein temperatures are given in degrees centigrade and parts are by weight unless otherwise indicated.

EXAMPLE 1

4-Chloro-2-thizaolesulfonamide (IV; Q=Q-3, $R_3$=Cl)

A. Benzylmercaptan (24.8 g) was added dropwise to a solution of 10.8 of sodium methoxide in 100 ml ethanol. After stirring 15 minutes, the ethanolic solution of sodium benzylmercaptide was added dropwise to a solution of 30.8 g 2,4-dichlorothiazole [prepared by the method of P. Reynaud et al., *Bull. Soc. Chim. France*, 1735 (1962)], resulting in a temperature increase of 28° to 48°. When the exotherm subsided, the suspension was refluxed 1 hour, then the solvent was evaporated. Cold water (300 ml) was added to the oily residue, and the aqueous mixture was extracted with methylene chloride. The organic solution was washed with water, followed by saturated brine, then dried over magnesium sulfate, filtered and the solvent evaporated to give 43.8 g of 4-chloro-2-phenylmethylthiothiazole as a brown oil.

B. A mixture of 43.8 g of 4-chloro-2-phenylthiothiazole, 225 ml acetic acid and 25 ml water was cooled to 4° and 29 ml of liquid chlorine was added dropwise while maintaining the temperature below 7°. When the addition of chlorine was complete, the light yellow solution was stirred 15 minutes at 0° prior to being poured into 1200 ml ice-water. The aqueous mixture was extracted with ether; the organic solution was washed with water, then dried over magnesium sulfate, filtered, and the solvent evaporated. The residual yellow oil was dissolved in 200 ml of tetrahydrofuran, and 50 ml of ammonium hydroxide was added dropwise at 25°-30°. The brown reaction mixture was stirred 1 hour at ambient temperature. The reaction mixture was concentrated, diluted with 200 ml wat er and acidified with acetic acid. The aqueous mixture was extracted with methylene chloride. The organic solution was washed with water, dried over magnesium sulfate, filtered, and the solvent evaporated. Trituration of the resulting oily solid with 300 ml hexane, filtration and washing with hexane gave 7.7 g of the title compound, m.p. 137°-141.5°.

NMR (CDCl$_3$/DMSO-d$_6$): δ 7.5 (s, 1H, 5-CH) and 7.7 (broad s, 2H, SO$_2$NH$_2$). IR: 3.06 and 3.28μ (SO$_2$NH$_2$).

EXAMPLE 2

N-[(4,6-Dimethoxypyrimidin-2-yl)-aminocarbonyl]-4-chloro-2-thiazolesulfonamide (I; Q=Q-3, R$_3$=Cl, R$_4$=H, Z=CH, X=Y=OCH$_3$)

To a suspension of 1.6 g of 4-chloro-2-thiazolesulfonamide in 100 ml methylene chloride under a nitrogen atmosphere, 4.4 ml of a 2.0M solution of trimethylaluminum in toluene was added slowly via a syringe. The reaction mixture was stirred 10 minutes; 1.9 g of methyl N-(4,6-dimethoxypyrimidin-2-yl)carbamate was added, and the reaction mixture refluxed for 18 hours. The reaction mixture was cooled to 0°, and 55 ml of 5% hydrochloric acid was added dropwise giving a flocculant solid. The reaction mixture was extracted with 100 ml of ethyl acetate. The organic solution was washed wtih brine, dried over magnesium sulfate, filtered and the solvent evaporated. The resulting tan solid was slurried in 1-chlorobutane, collected, washed with hexane and dried giving 1.25 g of the title compound as a white solid, m.p. 182°–183°(d). IR: 2.98 and 3.25μ (NH), 5.80μ (C=O).

NMR (CDCl$_3$/DMSO-d$_6$): δ 3.90 (s, 6H, OCH$_3$), 5.9 (s, 1H, pyrimidine CH), 7.95 (s, 1H, triazole CH) and 11.2 (s, 1H, NH).

Calcd. for C$_{10}$H$_{10}$ClN$_5$O$_5$S$_2$: C-31.62, H-2.66, N-18.43. Found: C-31.8, H-2.7, N-18.5 C-31.8, H-2.7, N-18.4.

EXAMPLE 3

4-Thiazolesulfonamide (IV; Q=Q-1, R=R$_1$=H)

A. Benzylmercaptan (24.8 g) was added slowly to a solution of 10.8 g of sodium methoxide in 100 ml ethanol. After 10 minutes, the reaction mixture was heated to 65° and a solution of 23.8 g of 4-chlorothiazole [prepared by the method of P. Reynaud et al., *Bull. Soc. Chim. France*, 1735 (1962)] in 25 ml ethanol was added dropwise. When addition was complete, the reaction mixture was refluxed 36 hours. The reaction mixture was cooled, and the bulk of the solvent evaporated. Cold water (300 ml) was added to the residue, and the aqueous mixture was extracted with 200 ml ether followed by 200 ml methylene chloride. The combined organic solution was washed with brine, dried over magnesium sulfate, filtered and the solvent evaporated. Distillation of the resulting yellow oil gave 15.6 g of 4-(phenylmethylthio)thiazole, bp 122–134 (0.6 mm).

B. A mixture of 15.6 g of 4-(phenylmethylthio)thiazole in 75 ml acetic and 25 ml water was cooled to ~5° and 12.0 ml of liquid chlorine was added dropwise at ~5°. When the addition was complete, the yellow solution was stirred 20 minutes at 0°, then poured into 500 ml ice water. The aqueous mixture was extracted with methylene chloride. The organic solution was washed twice with water, dried over magnesium sulfate, filtered, and the solvent evaporated to give a yellow oil that partially crystallized on colling. The crude sulfonyl chloride was dissolved in 100 ml of tetrahydrofuran, and 12.0 ml of ammonium hydroxide added dropwise at 5°–10°. The resulting brown suspension was allowed to warm to ambient temperature, then concentrated to an oily solid. Addition of 200 ml water and 100 ml methylene chloride to the oily solid gave a solid at the interface. The solid was collected, washed with water followed by hexane and dried giving 3.8 g of the title compound as brown solid, m.p. 142°–146.5°. IR: 3.1 and 3.2μ (SO$_2$NH$_2$).

NMR (CDCl$_3$/DMSO-d$_6$): δ 7.15 (broad s, 2H, SO$_2$NH$_2$), 8.1 (d, 1H, CH) and 8.6 (d, 1H, CH).

EXAMPLE 4

N-[(4-methoxy-6-methylpyrimidin-2-yl)aminocarbonyl]-4-thiazolesulfonamide (I; Q=Q-1, R=R$_1$=H, Z=CH, X=OCH$_3$, Y=CH$_3$)

By using the procedure described in Example 2, the reaction of 0.98 of g of 4-thiazolesulfonamide with 1.3 g of methyl N-(4-methoxy-6-methylpyrimidin-2-yl)-carbamate in the presence of 3.3 ml of a 2.0M solution of trimethylaluminum in toluene, there was obtained 0.7 g of the title compound as an off-white solid, m.p. 196°–200°(d). IR: 5.89μ (C=O).

NMR (CDCl$_3$/DMSO-d$_6$): δ 2.48 (s, 3H, CH$_3$), 3.90 (s, 3H, OCH$_3$), 6.45 (s, 1H, pyrimidine CH), 8.67 (d, 1H, thiazole CH), 9.26 (d, 1H, thiazole CH), 10.5 (s, 1H, NH) and 13.2 (s, 1H, NH).

EXAMPLE 5

5-Ethoxy-2-methyl-4-thiazolesulfonamide (IV; Q=Q-1, R=CH$_3$, R$_1$=OC$_2$H$_5$)

A solution of 11.1 g of 4-bromo-5-ethoxy-2-methylthiazole [prepared by the method of D. S. Tarbell et al., *J. Amer. Chem. Soc.*, 72, 3138 (1950) in 50 ml ether was cooled to −60°, and 35.9 ml of a 1.7M solution of n-butyl lithium in hexane was added dropwise while maintaining the temperature below −45°. The resulting heavy yellow-brown suspension was diluted with an additional 25 ml ether and stirred 20 minutes at a temperature of −50° to −30°. The etheral suspension of the lithiothiazole was added via syringe to a solution of 8.0 ml sulfuryl chloride in 50 ml hexane, while maintaining the temperature between −30° and −20°. After the suspension was stirred 15 minutes at −30°, it was allowed to warm to −5° and stirred 3.5 hours. The reaction mixture was poured into 500 ml ice-water. The two-phase suspension was extracted twice with ether. The combined organic solution was washed with water and brine, then dried over magneisum sulfate, filtered, and the solvent evaporated. The resulting oily solid was dissolved in 150 ml of tetrahydrofuran; the solution was cooled to 0°, and 6.7 ml of ammonium hydroxide added dropwise. The brown suspension was allowed to warm to ambient and stirred 3 hours. The solvent was evaporated, and the residual black oil partitioned between methylene chloride and water. The organic solution was washed with water followed by brine, then stirred 0.5 hour with magnesium sulfate and charcoal. The mixture was filtered through Celite@ and the solvent was evaporated. Trituration of the resulting brown oily solid with 1-chlorobutane gave 4.2 g of the title compound as a tan solid, m.p. 118°–120°. IR: 3.05 and 3.15μ (SO$_2$NH$_2$).

NMR (CDCl$_3$/DMSO-d$_6$): δ 1.25 (t, 3H, CH$_3$), 2.60 (s, 3H, CH$_3$), 4.22 (q, 2H, OCH$_2$) and 6.10 (broad s, 2H, SO$_2$NH$_2$).

EXAMPLE 6

5-Ethoxy-N-[(4,6-dimethoxypyrimidin-2-yl)aminocarbonyl]-2-methyl-4-thiazolesulfonamide (I; Q=Q-1, R=CH$_3$, R$_1$=OC$_2$H$_5$, Z=CH, X=Y=OCH$_3$)

By employing the procedure described in Example 2, the reaction of 1.33 g of 5-ethoxy-2-methyl-4- thiazolesulfonamide with 1.4 g of methyl N-(4,6-dimethoxypyrimidin-2-yl)carbamate in the presence of 3.3 ml of a 2.0M solution of trimethylaluminum, there was obtained 1.2 g of the title compound, m.p. 140°–143°. IR: 1710 cm$^{-1}$ (C=O).

NMR (CDCl$_3$): δ 1.5 (t, 3H, CH$_3$), 2.6 (s, 3H, CH$_3$), 3.95 (s, 6H, OCH$_3$), 4.3 (q, 2H, OCH$_2$), 5.8 (s, 1H, pyrimidine CH$_3$), 7.5 (broad s, 1H, NH) and 13.0 (s, 0.67H, NH).

EXAMPLE 7

Methyl 5-(aminosulfonyl)-4-thiazolecarboxylate (IV; Q=Q-2, R=H, R$_2$=CO$_2$CH$_3$)

A. A solution of 31.3 g of potassium t-butoxide in 280 ml of tetrahydrofuran was cooled to −50° and a solution of 27.7 g of methyl isocyanoacetate in 230 ml of tetrahydrofuran was added dropwise at −50° to −40°. The resulting brown suspension was stirred 15 minutes then cooled to −78°, then a solution of 16.8 ml of carbon disulfide in 225 ml tetrahydrofuran was added dropwise while maintaining the temperature below −50°. The pinkish-brown thick suspension was allowed to warm to −15° to 10° over 15 to 20 minutes. To the reaction mixture, a solution of 33.3 ml of benzyl bromide in 140 ml tetrahydrofuran was added dropwise at −15° to −5°. The reaction mixture was stirred at ambient temperature for 30 minutes, refluxed for 20 minutes, then cooled and the bulk of the solvent evaporated. To the oily residue, 1000 ml ice-water was added. After several minutes, the product soldified. The tan solid was collected, washed twice with water, followed by hexane and dried giving 68.8 g of methyl 5-(phenylmethylthio)-4-thiazolecarboxylate, m.p. 90°–92°.

B. A solution of 39.8 g of methyl 5-(phenylmethylthio)-4-thiazolecarboxylate in 225 ml acetic acid and 25 ml water was cooled to 3°, and 23.9 ml of liquid chlorine was added dropwise below 10°. The yellow-brown solution was stirred 45 minutes at 5°–10° before being poured into 1200 ml of ice-water to give a yellow oil which partially solidified on standing. The crude reaction product was collected, washed with water, then four times with hexane and dried to give 29.4 g of methyl 5-(chlorosulfonyl)-4-thiazolecarboxylate, m.p. 94°–97.5°.

C. A solution of 28.9 g of methyl 5-(chlorosulfonyl)-4-thiazolecarboxylate in 150 ml tetrahydrofuran was cooled to 0° and 6.6 ml of liquid ammonia was added dropwise at 0°–10°. The suspension was allowed to warm to ambient temperature and stirred 1 hour. The reaction mixture was filtered, the ammonium chloride washed with tetrahydrofuran, and the solvent evaporated from the filtrate. The residual solid was slurried in hexane, collected and dried to give 25.0 g of the title compound, m.p. 138°–140°. IR: 301 and 3.1μ (SO$_2$NH$_2$) and 5.8μ (C=O).

NMR (CDCl$_3$/DMSO-d$_6$): δ 4.0 (s, 3H, OCH$_3$), 7.2 (broad s, 2H, SO$_2$NH$_2$) and 9.0 (s, 1H, thiazole CH).

EXAMPLE 8

5-Methoxycarbonyl-4-thiazolesulfonyl isocyanate (II; Q=Q$_1$, R$_1$=CO$_2$CH$_3$, R=H)

A mixture of 11.1 g of 5-(aminosulfonyl)-4-thiazolecarboxylate, 5.6 ml of butyl isocyanate and 0.17 g of diaza[2.2.2]bicyclooctane in 150 ml xylene was heated to reflux. Phosgene (4.2 ml) was added dropwise in small portions to the reaction mixture, while maintaining the temperature above 130°. When the last 0.5 ml of phosgene was added, the reaction temperature dropped to 124°. The reaction mixture refluxed 1 hour, then the dry-ice condenser replace with a water condenser, and the mixture refluxed 30 minutes under a slow stream of nitrogen. The reaction mixture cooled, filtered twice under nitrogen, and the solvent evaporated from the filtrate to give the title sulfonyl isocyanate as thick yellow oil. IR: 4.45μ (SO$_2$NCO).

The crude sulfonyl isocyanate was dissolved in 50 ml of methylene chloride for reactions with amino heterocycles.

EXAMPLE 9

Methyl 5-[[(4,6-dimethoxypyrimidin-2-yl)aminocarbonyl)aminosulfonyl]-4-thiazolecarboxylate (I; Q=Q-1; R$_1$=CO$_2$CH$_3$, R=H, Z=CH, X=Y=OCH$_3$)

To a stirred suspension of 0.78 g of 4,6-dimethoxy-2-pyrimidinamine and a crystal of diaza[2.2.2]bicyclooctane in 5 ml of methylene chloride was added 1l of the methylene chloride solution prepared in Example 8. After the addition, a clear solution developed; a precipitate began forming after approximately 30 minutes. The suspension was stirred overnight at ambient temperature. The solid was collected, washed with 1-chlorobutane and dried giving 1.2 g of the title compound, m.p. 172°–174°(d). IR: 1721 and 1790 cm$^{-1}$ (2×C=O).

NMR (CDCl$_3$/DMSO-d$_6$): δ 3.97 (s, 3H, OCH$_3$), 4.02 (s, 6H, OCH$_3$), 5.8 (s, 1H, pyrimidine CH), 9.1 (s, 1H, thiazole CH), 10.0 (broad s, 1H, NH) and 13.1 (broad s, 1H, NH).

EXAMPLE 10

Ethyl 4-(aminosulfonyl)-2-methyl-5-thiazole carboxylate (IV; Q=Q-1, R=CH$_3$, R$_1$=CO$_2$C$_2$H$_5$)

A. A 5.05 g portion of 50% sodium hydride in mineral oil was washed with hexane and suspended in 100 ml of dimethylformamide. To this suspension, a solution of 19.57 g ethyl 4-hydroxy-2-methyl-5-thiazolecarboxylate in 100 ml of dimethylformamide was added dropwise resulting in the formation of a heavy yellow gel. The reaction mixture was diluted with 75 ml dimethylformamide and stirred for 30 minutes. A solution of 14.23 g of dimethylthiocarbamyl chloride in 50 ml dimethylformamide was added dropwise to the thick slurry, then the reaction mixture was heated at 85°–95° for 45 minutes. The resulting brown suspension was cooled and poured into a cold solution of 5.7 g sodium hydroxide in 1200 ml water. The aqueous mixture was extracted once with benzene and twice with ether. The combined organic extracts were washed twice with water followed by brine, then dried over magnesium sulfate, filtered and the solvent evaporated giving an oil that partially crystallized. The crude reaction product was slurried in hexane, collected and dried giving 13.1 g of ethyl 4-[(dimethylamino)thioxomethyloxy]-2-methyl-5-thiazolecarboxylate, m.p. 87°–90°.

B. A 12.3 g sample of the compound of Part A was heated at 170°–195° under a nitrogen atmosphere for 1.5 hour. The dark reaction mixture was cooled and dissolved in methylene chloride. The solvent was evaporated to give a black oil which crystallized on scratching. Recrystallization from hexane-ethyl acetate gave 9.2 g of ethyl 4-[(dimethylamino)carbonylthio]-2-methyl-5-thiazolecarboxylate, m.p. 84.5°–85.5°.

C. A 21.5 g sample of the compound prepared as in Part B was added to a solution of 2.7 g of sodium in 200 ml ethanol, and the reaction mixture stirred overnight at ambient temperature. The tan suspension was concentrated, the residue was dissolved in 500 ml water and the aqueous solution acidified with cold, dilute hydrochloric acid. The aqueous mixture was extracted with methylene chloride; the organic solution was dried over magnesium sulate, filtered and the solvent evaporated. Cold water (200 ml) was added to the oily solid; the resulting solid was collected, washed with water and dried giving 13.4 g of ethyl 4-mercapto-2-methyl-5-thiazolecarboxylate, m.p. 62°–66°.

D. A solution of 14.4 g of the compound, prepared as in Part B, in a mixture of 80 ml of acetic acid and 20 ml water was cooled to 0°, and 11.3 ml of liquid chlorine was added dropwise at 0°–8°. The yellow-brown solution was stirred 30 minutes at approximately 5°, then poured into 500 ml water. The aqueous mixture was extracted twice with ether; the organic solution was washed twice with water, dried over magnesium sulfate, filtered and the solvent evaporated to give an oil. The crude sulfonyl chloride was dissolved in 100 ml tetrahydrofuran and the solution cooled to 5°. Ammonium hydroxide (10.4 ml) was added dropwise; the reaction mixture had a pH <7. More ammonium hydroxide (4.4 ml) was added; the reaction mixture was allowed to warm to ambient temperature and stirred 2 hours. The solvent was evaporated and 300 ml cold water was added to the residual oily solid. The resulting solid was collected, washed with water and dried giving 8.1 g of the title sulfonamide, m.p. 129°–131.5°. IR: 3380 and 3225 cm$^{-1}$ (SO$_2$NH$_2$), 1705 cm$^{-1}$ (C=O).

EXAMPLE 11

5-Ethoxycarbonyl-2-methyl-4-thiazolesulfonyl isocyanate (II; Q=Q-1, R=CH$_3$, R$_1$=CO$_2$C$_2$H$_5$)

A mixture of 7.5 g of the sulfonamide prepared in Example 9, 3.4 ml butyl isocyanate, and a few crystals of diaza[2.2.2]bicyclooctane in 85 ml xylene was heated to 136° and 2.3 ml of phosgene was added dropwise. The reaction temperature had dropped to 126° when addition of phosgene was complete. The reaction mixture was refluxed 30 minutes; the dry-ice condenser replaced with a water condenser, and the mixture refluxed an additional 30 minutes under a slow stream of nitrogen. The reaction mixture was cooled and filtered under nitrogen. Evaporation of the solvent gave the title sulfonyl isocyanate as a yellow-brown oil. IR: 2240 cm$^{-1}$ (SO$_2$NCO) and 1760 cm$^{-1}$ (C=O).

The crude isocyanate was dissolved in 25 ml of methylene for reaction with heterocyclic amines.

EXAMPLE 12

Ethyl 4-[[(4-methoxy-6-methyl-1,3,5-triazin-2-yl)aminocarbonyl]aminosulfonyl]-2-methyl-5-thiazolecarboxylate (I; Q=Q-2, R=CH$_3$, R$_2$=CO$_2$C$_2$H$_5$, Z=N, X=OCH$_3$, Y=CH$_3$)

A 7 ml portion of the methylene chloride solution of the sulfonyl isocyanate, prepared in Example 10, was added to a stirred suspension of 0.35 g of 4-methoxy-6-methyl-1,3,5-triazin-2-amine and a crystal of diaza[2.2.2-]bicyclooctane in methylene chloride. The reaction mixture was stirred overnight. The clear solution was concentrated to a yellow-brown oil. On lengthy trituration with ether, a solid was obtained which was collected, washed with ether and dried to give 0.48 g of the title compound, m.p. 126°–130°. IR: 1725 and 1720 cm$^{-1}$ (2×C=O).

NMR (CDCl$_3$): δ1.35 (t, 3H, CH$_3$), 2.6 (s, 3H, CH$_3$), 2.75 (s, 3H, CH$_3$), 4.15 (s, 3H, OCH$_3$), 4.4 (q, 2H, OCH$_2$), 8.2 (broad s, 1H, NH) and 12.6 (broad s, 1H, NH).

By the methods described in Examples 1–12, or modifications thereof, the compounds of Tables I–III may be prepared.

TABLE I

![structure]

| R | R$_1$ | X | Y | Z | m.p. (°C.) |
|---|---|---|---|---|---|
| H | H | OCH$_3$ | OCH$_3$ | CH | 201–203° |
| H | H | CH$_3$ | CH$_3$ | CH | |
| H | H | CH$_3$ | OCH$_3$ | N | |
| H | H | OCH$_3$ | OCH$_3$ | N | |
| H | H | CH$_3$ | CH$_3$ | N | |
| H | H | OC$_2$H$_5$ | CH$_3$ | CH | |
| H | H | CH$_2$OCH$_3$ | OCH$_3$ | CH | |
| CH$_3$ | OC$_2$H$_5$ | CH$_3$ | OCH$_3$ | CH | 157–160° |
| CH$_3$ | OC$_2$H$_5$ | CH$_3$ | CH$_3$ | CH | 175–178° |
| CH$_3$ | OC$_2$H$_5$ | OCH$_3$ | OCH$_3$ | CH | 140–143° |
| CH$_3$ | OC$_2$H$_5$ | CH$_3$ | OCH$_3$ | N | |
| CH$_3$ | OC$_2$H$_5$ | CH$_3$ | CH$_3$ | N | |
| CH$_3$ | OC$_2$H$_5$ | OCH$_3$ | OCH$_3$ | N | |
| H | OCH$_3$ | OCH$_3$ | OCH$_3$ | CH | |
| H | OCH$_3$ | CH$_3$ | CH$_3$ | CH | |
| H | OCH$_3$ | OC$_2$H$_5$ | OCH$_3$ | CH | |
| H | OCH$_3$ | OCH$_3$ | OCH$_3$ | CH | |
| H | OCH$_3$ | OCH$_3$ | CH$_3$ | N | |
| H | OCH$_3$ | OCH$_3$ | CH$_3$ | N | |
| H | OCH$_3$ | CH$_2$OCH$_3$ | OCH$_3$ | N | |
| H | OC$_3$H$_7$ | OCH$_3$ | OCH$_3$ | CH | |
| H | CH$_3$ | CH$_3$ | OCH$_3$ | N | |
| H | C$_2$H$_5$ | CH$_3$ | CH$_3$ | CH | |
| H | C$_3$H$_7$ | OCH$_3$ | OCH$_3$ | CH | |
| CH$_3$ | SCH$_3$ | CH$_3$ | OCH$_3$ | CH | |
| CH$_3$ | OC$_2$H$_5$ | OCF$_2$H | CH$_3$ | CH | |
| CH$_3$ | OC$_2$H$_5$ | OCF$_2$H | CH$_3$O | CH | |
| CH$_3$ | OC$_2$H$_5$ | OCF$_2$H | CH | | |
| CH$_3$ | SC$_2$H$_5$ | OCH$_3$ | OCH$_3$ | N | |
| CH$_3$ | SC$_3$H$_7$ | CH$_3$ | OCH$_3$ | N | |
| CH$_3$ | CO$_2$C$_2$H$_5$ | CH$_3$ | CH$_3$ | CH | 150–153° |
| CH$_3$ | CO$_2$C$_2$H$_5$ | CH$_3$ | OCH$_3$ | CH | 87–97° |
| CH$_3$ | CO$_2$C$_2$H$_5$ | OCH$_3$ | OCH$_3$ | CH | 121–123° |
| CH$_3$ | CO$_2$C$_2$H$_5$ | CH$_3$ | OCH$_3$ | N | 126–130° |
| CH$_3$ | CO$_2$C$_2$H$_5$ | OCH$_3$ | OCH$_3$ | N | 140–145° |
| CH$_3$ | CO$_2$C$_2$H$_5$ | CH$_2$OCH$_3$ | OCH$_3$ | N | |
| CH$_3$ | CO$_2$C$_2$H$_5$ | OC$_2$H$_5$ | CH$_3$ | N | |
| H | CO$_2$CH$_3$ | CH$_3$ | CH$_3$ | CH | |
| H | CO$_2$CH$_3$ | CH$_3$ | OCH$_3$ | CH | |
| H | CO$_2$CH$_3$ | OCH$_3$ | OCH$_3$ | CH | |
| H | CO$_2$CH$_3$ | OCH$_3$ | CH$_3$ | N | |
| H | CO$_2$CH$_3$ | OCH$_3$ | OCH$_3$ | N | |
| H | CO$_2$C$_3$H$_7$ | OCH$_3$ | OCH$_3$ | CH | |
| C$_2$H$_5$ | H | CH$_3$ | OCH$_3$ | N | |
| C$_3$H$_7$ | SCH$_3$ | CH$_3$ | OCH$_3$ | CH | |
| CH$_3$ | OCH$_3$ | OCF$_2$H | CH$_3$ | CH | |
| CH$_3$ | OCH$_3$ | C$_2$H$_5$ | OCH$_3$ | CH | |
| H | H | C$_2$H$_5$ | OCH$_3$ | N | |
| H | H | C$_2$H$_5$ | OCH$_3$ | CH | |
| CH$_3$ | OC$_2$H$_5$ | C$_2$H$_5$ | OCF$_2$H | CH | |
| H | H | OCH$_3$ |  | N | |
| H | H | CH$_3$ |  | CH | |

TABLE I-continued

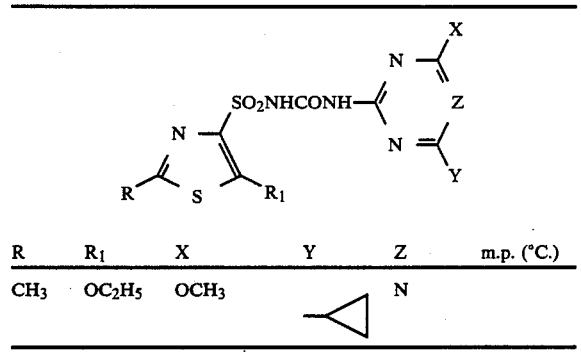

| R | R₁ | X | Y | Z | m.p. (°C.) |
|---|-----|---|---|---|---|
| $CH_3$ | $OC_2H_5$ | $OCH_3$ | ◁ | N | |

TABLE II

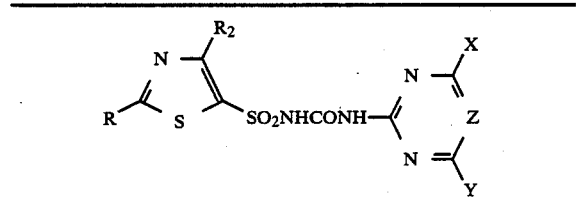

| R | R₂ | X | Y | Z | m.p. (°C.) |
|---|-----|---|---|---|---|
| $CH_3CONH$ | $CH_3$ | $CH_3$ | $CH_3$ | CH | |
| $CH_3CONH$ | $CH_3$ | $CH_3$ | $OCH_3$ | CH | |
| $CH_3CONH$ | $CH_3$ | $OCH_3$ | $OCH_3$ | CH | 191–195°(d) |
| $CH_3CONH$ | $CH_3$ | $CH_3$ | $CH_2OCH_3$ | CH | |
| $CH_3CONH$ | $CH_3$ | $CH_3$ | $CH_3$ | N | |
| $CH_3CONH$ | $CH_3$ | $OCH_3$ | $OCH_3$ | N | |
| $CH_3CONH$ | $CH_3$ | $OCH_3$ | $OC_2H_5$ | N | |
| $CH_3CONH$ | $CH_3$ | $CH_3$ | $OCH_3$ | N | |
| H | $C_2H_5$ | $OCH_3$ | $OCH_3$ | CH | |
| H | $C_3H_7$ | $CH_3$ | $OCH_3$ | N | |
| $CH_3$ | $OCH_3$ | $OCH_3$ | $OCH_3$ | CH | |
| $CH_3$ | $OC_2H_5$ | $CH_3$ | $OCH_3$ | CH | |
| $CH_3$ | $OC_3H_7$ | $CH_3$ | $OCH_3$ | CH | |
| $C_2H_5$ | $SCH_3$ | $OCH_3$ | $OCH_3$ | N | |
| $C_3H_7$ | H | $CH_3$ | $OCH_3$ | CH | |
| H | $CO_2CH_3$ | $CH_3$ | $CH_3$ | CH | 174–175°(d) |
| H | $CO_2CH_3$ | $OCH_3$ | $CH_3$ | CH | 179–180°(d) |
| H | $CO_2CH_3$ | $OCH_3$ | $OCH_3$ | CH | 172–174°(d) |
| H | $CO_2CH_3$ | $CH_3$ | $OCH_3$ | N | 166–169°(d) |
| H | $CO_2CH_3$ | $OCH_3$ | $OCH_3$ | N | 177–178°(d) |
| H | $CO_2C_2H_5$ | $OCH_3$ | $CH_3$ | CH | |
| H | $CO_2C_3H_7$ | $CH_3$ | $OCH_3$ | CH | |
| $CH_3CONH$ | $CH_3$ | $OCF_2H$ | $CH_3$ | CH | |
| H | H | $CH_3$ | $OCH_3$ | N | |
| H | H | $OCH_3$ | $OCH_3$ | N | |
| H | H | $CH_3$ | $OCH_3$ | CH | |
| H | H | $OCH_3$ | $OCH_3$ | CH | |
| $CH_3CONH$ | $CF_3$ | $CH_3$ | $OCH_3$ | CH | |
| $CH_3CONH$ | $NO_2$ | $OCH_3$ | $OCH_3$ | CH | |
| $CH_3CONH$ | Br | $OCH_3$ | $OCH_3$ | CH | |
| $CH_3CONH$ | Cl | $OCH_3$ | $OCH_3$ | CH | |
| $CH_3$ | $CO_2CH_3$ | $OCH_3$ | ◁ | N | |
| $CH_3$ | $CO_2CH_3$ | $CH_3$ | ◁ | CH | |

TABLE III

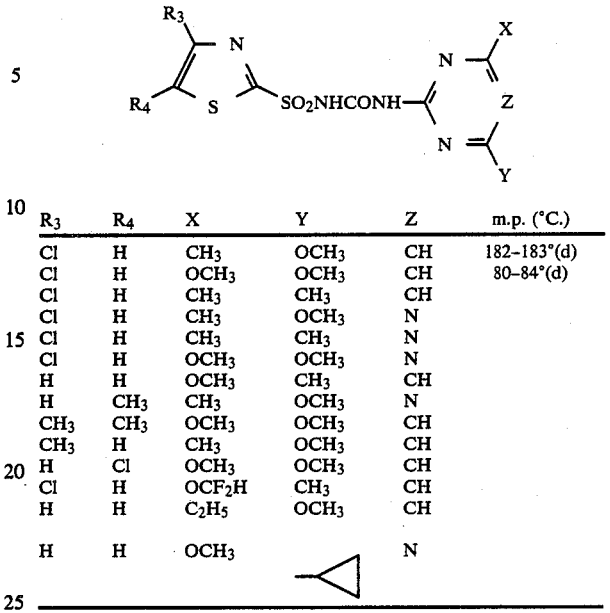

| R₃ | R₄ | X | Y | Z | m.p. (°C.) |
|----|----|---|---|---|---|
| Cl | H | $CH_3$ | $OCH_3$ | CH | 182–183°(d) |
| Cl | H | $OCH_3$ | $OCH_3$ | CH | 80–84°(d) |
| Cl | H | $CH_3$ | $CH_3$ | CH | |
| Cl | H | $CH_3$ | $OCH_3$ | N | |
| Cl | H | $CH_3$ | $CH_3$ | N | |
| Cl | H | $OCH_3$ | $OCH_3$ | N | |
| H | H | $OCH_3$ | $CH_3$ | CH | |
| H | $CH_3$ | $CH_3$ | $OCH_3$ | N | |
| $CH_3$ | $CH_3$ | $OCH_3$ | $OCH_3$ | CH | |
| $CH_3$ | H | $CH_3$ | $OCH_3$ | CH | |
| H | Cl | $OCH_3$ | $OCH_3$ | CH | |
| Cl | H | $OCF_2H$ | $CH_3$ | CH | |
| H | H | $C_2H_5$ | $OCH_3$ | CH | |
| H | H | $OCH_3$ | ◁ | N | |

FORMULATIONS

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE IV

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J., but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, N.Y., 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, Jun. 23, 1959, Col. 3, line 66 through Col. 5, line 17 and Examples 1–4;

G. C. Klingman, "Weed Control as a Science", John Wiley and Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 13

| Wettable Powder | |
|---|---|
| N-[(4-methoxy-6-methylpyrimidin-2-yl)aminocarbonyl]-4-thiazolesulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 14

| Wettable Powder | |
|---|---|
| N-[(4,6-dimethoxypyrimidin-2-yl)aminocarbonyl]-4-thiazolesulfonamide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 15

| Granule | |
|---|---|
| Wettable Powder of Example 14 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 16

| Extruded Pellet | |
|---|---|
| N-[(4-methoxy-6-methylpyrimidin-2-yl)aminocarbonyl]-4-thiazolesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 17

| Low Strength Granule | |
|---|---|
| N-[(4,6-dimethoxypyrimidin-2-yl)aminocarbonyl]-4-thiazolesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 18

| Granule | |
|---|---|
| N-[(4,6-dimethoxypyrimidin-2-yl)aminocarbonyl]-4-thiazolesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 19

| Low Strength Granule | |
|---|---|
| N-[(4-methoxy-6-methylpyrimidin-2-yl)aminocarbonyl]-4-thiazolesulfonamide | 1% |
| N,N-dimethylformamide | 9% |
| attapulgite granules (U.S.S. 20-40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 20

| Aqueous Suspension | |
|---|---|
| N-[(4,6-dimethoxypyrimidin-2-yl)aminocarbonyl]-4-thiazolesulfonamide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 21

| Solution | |
|---|---|
| N-[(4-methoxy-6-methylpyrimidin-2-yl)aminocarbonyl]-4-thiazolesulfonamide, sodium salt | 5% |
| water | 95% |

The salt is added directly to the water with stirring to produce the solution, which may then be packaged for use.

EXAMPLE 22

| High Strength Concentrate | |
|---|---|
| N-[(4,6-dimethoxypyrimidin-2-yl)aminocarbonyl]-4-thiazolesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 23

| Wettable Powder | |
|---|---|
| N-[(4-methoxy-6-methylpyrimidin-2-yl)aminocarbonyl]-4-thiazolesulfonamide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 24

| Wettable Powder | |
|---|---|
| N-[(4,6-dimethoxypyrimidin-2-yl)aminocarbonyl]-4-thiazolesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 25

| Oil Suspension | |
|---|---|
| N-[(4-methoxy-6-methylpyrimidin-2-yl)aminocarbonyl]-4-thiazolesulfonamide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 26

| Dust | |
|---|---|
| N-[(4,6-dimethoxypyrimidin-2-yl)aminocarbonyl]-4-thiazolesulfonamide | 10% |
| attapulgite | 10% |
| pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 27

| Oil Suspension | |
|---|---|
| N-[(4-methoxy-6-methylpyrimidin-2-yl)aminocarbonyl]-4-thiazolesulfonamide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 28

| Wettable Powder | |
|---|---|
| N-[(4,6-dimethoxypyrimidin-2-yl)aminocarbonyl]-4-thiazolesulfonamide | 20% |
| soldium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

UTILITY

Test results indicate that the compounds of the present invention are active herbicides. They should have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, many of the subject compounds should be useful for the selective pre- or post-emergence weed control in crops, such as wheat and barley.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for selective weed control or for situations where only short-term persistence is required. The compounds are applied to the locus of the plants to be controlled, i.e., to the soil in which seeds are planted for pre-emergence control or to the plants themselves for post-emergence control.

The compounds of the invention may be used in combination with any other commercial herbicide examples of which are those of the triazine, triazole, uracil, urea, amide, diphenylether, carbamate and bipyridylium types.

The herbicidal properties of the subject compounds were discovered in a number of greenhouse tests. The test procedures and results follow.

TEST A

Seeds of crabgrass (Digitaria sp.), barnyard-grass (Echinochloa crusgalli), wild oats (Avena fatua), sicklepod (Cassia obtusifolia), morningglory (Ipomea sp.), cocklebur (Xanthium sp.), sorghum, corn, soybean, sugar beet, rice, wheat and purple nutsedge (Cyperus rotundus) tubers were planted and treated pre-emergence with the test chemicals dissolved in a nonphytotoxic solvent. At the same time, these crop and weed species, along with cotton and bush bean, were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis/necrosis;
E=emergence inhibition;
G=growth retardation;
H=formative effect;
P=terminal bud kill;
S=albinism;
X=axillary stimulation; and
6Y=abscised buds or flowers.

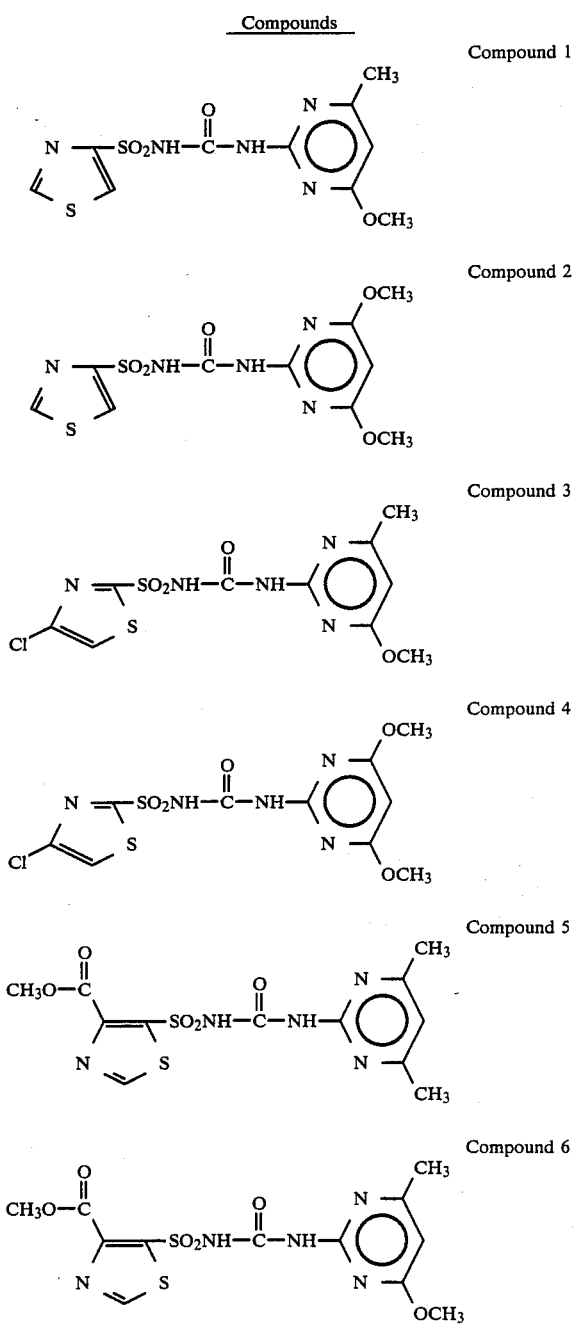

Compounds

-continued
Compounds
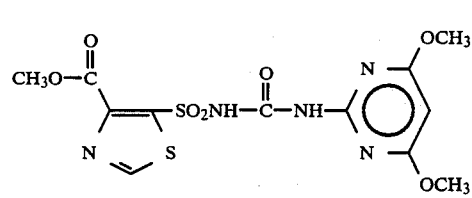
Compound 7
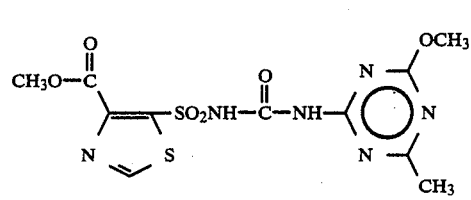
Compound 8
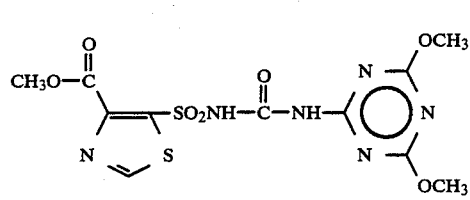
Compound 9
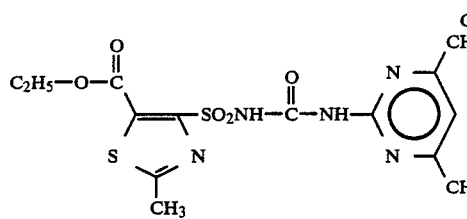
Compound 10
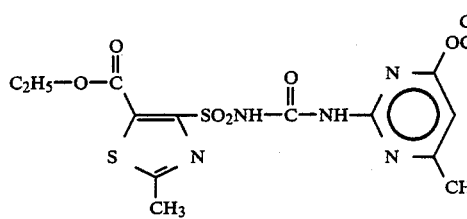
Compound 11
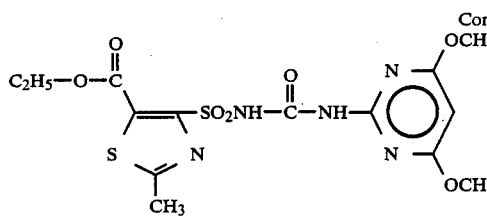
Compound 12
-continued
Compounds
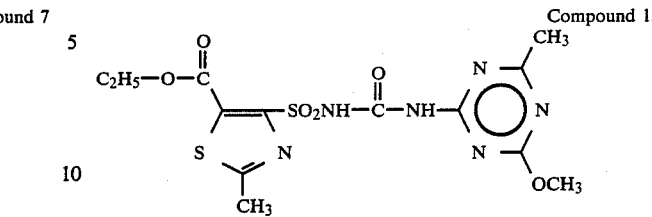
Compound 13
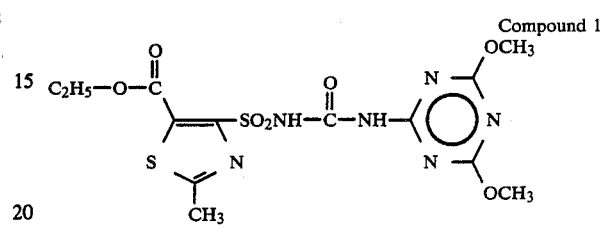
Compound 14
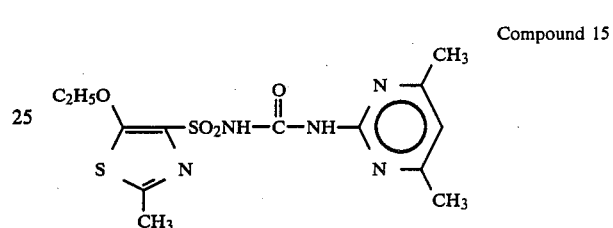
Compound 15
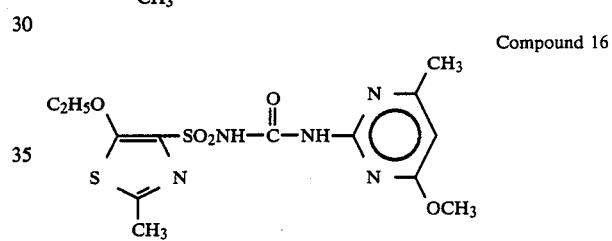
Compound 16
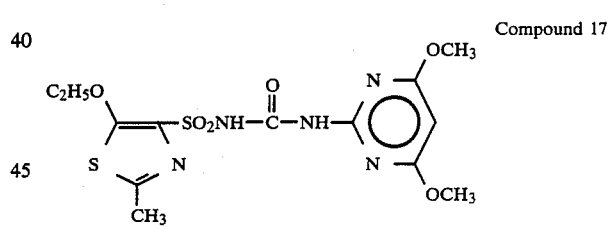
Compound 17
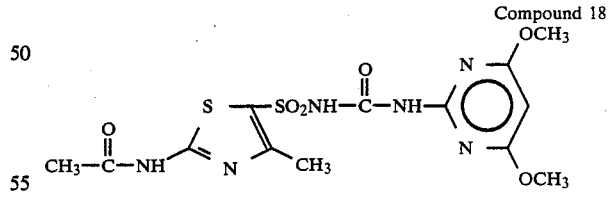
Compound 18

TABLE A

| | Cmpd. 1 | Cmpd. 2 | Cmpd. 3 | Cmpd. 4 | Compound 5 | | Compound 6 | | Compound 7 | | Compound 8 | | Compound 9 | | Compound 10 | |
|---|---|---|---|---|---|---|---|---|---|---|---|---|---|---|---|---|
| Rate kg/ha | 0.05 | 0.05 | 0.05 | 0.05 | 0.4 | 2 | 0.05 | 0.4 | 0.05 | 0.4 | 0.05 | 0.4 | 2 | 0.05 | 0.4 | 2 | 0.4 |
| | POST-EMERGENCE | | | | | | | | | | | | | | | | |
| Bush bean | 4C,9G,6Y | 2C,5G,6Y | 5S,9G,6Y | 4C,5G,6Y | 2G | — | 6C,9G,6Y | 9C | 3C,5G,6Y | 9C | 0 | 0 | — | — | 1C | 4C,9G,6Y | 3C,9G,6Y |
| Cotton | 4C,9G | 3C,9G | 4C,5H,9G | 5C,9G | — | 4C,9G | — | — | — | 9H | 0 | 0 | — | — | — | 4C,5G | 3C,6G |
| Morningglory | 4C,9G | 3C,7G | 0 | 1C,3G | 2C,2H | 3C,6H | 4C,8H | 7C | 2C | 2C,9H | 0 | 0 | 1C | 3G | — | 3C | 5C,8G |
| Cocklebur | 5C,9G | 9C | 10C | 10C | 3C,7H | 5C,9H | 3C,8G | 9C | 3C,9H | 10C | 0 | 2C | 2C,5H | 1C | 0 | 3C,8H | 3C,8G |
| Sicklepod | 3C,9G | 4C,9G | 1C | 2H | 1C | 3C,3H | 1C | 2C | 2C | 1C,2G | 0 | 0 | 1C | 0 | 0 | 2C | 3C,9G |
| Nutsedge | 9G | 9G | 0 | 0 | 0 | 5G | 2C | 2C,7G | 2C | 3C,8G | — | — | 0 | 0 | 0 | 0 | 1C,3G |
| Crabgrass | 2C,6G | 2C,5G | 0 | 0 | 0 | 5G | 2C,7G | 2C,9H | 2C | 2C,5G | 0 | 0 | 0 | 0 | 1C,4G | 0 | 3C,8H |
| Barnyardgrass | 2C,9H | 4C,8H | 0 | 0 | 3H | 5C,9H | 3C,8H | 5C,9H | 2C,3H | 2C,9H | 0 | 1H | 5C,9H | 0 | 3C,9H | 1C | 1C,9G |
| Wild Oats | 2C,8G | 2C,9G | 0 | 0 | 0 | 0 | 0 | 0 | 0 | 0 | 0 | 0 | 0 | 0 | 0 | 1C | 3C,9G |
| Wheat | 1C,8G | 2C,9G | 3H | 1H | 2C,2H | 2C,6H | 2C,5H | 2C,9G | 2C,5H | 2C,6G | 0 | 0 | 2C,6G | 0 | 2G | 2C | 3C,9G |
| Corn | 4U,9G | 2U,9G | 3H | 5C,9G | 1H | 0 | 2C,8G | 2C,8G | 2C,3H | 3U,9G | 0 | 2H | 3U,9G | 0 | 8G | 1C,2G | 6C,9G |
| Soybean | 9C | 9C | 0 | 0 | 0 | 0 | 3C,8G | 3C,8G | 3G | 3C,6H | 0 | 0 | 1C | 0 | 0 | 2C,6G | 3C,8G |
| Rice | 5C,9G | 4C,9G | 0 | 5C,9G | 2C,5G | 4C,9G | 2C,8G | 2C,8G | 1C,3G | 4C,9H | — | 0 | 5C,9G | — | 3C,8G | 3C,9H | 3C,9G |
| Sorghum | 9G | 2C,9G | 2G | 0 | 0 | 3C,8H | 3C,7G | 3C,7G | 2C,4G | 3C,7H | 0 | 0 | 3C,8H | 0 | 1C,4H | 3C,8H | 5C,9G |
| Sugar beet | — | — | — | — | — | 5C,9G | — | — | — | — | — | — | 1C,2H | — | 0 | 9C | — |
| Cotton | — | — | — | — | — | 6G | — | — | — | — | — | — | — | — | — | — | — |
| | PRE-EMERGENCE | | | | | | | | | | | | | | | | |
| Morningglory | 9G | 8G | 6G | 5G | 0 | 9G | 8G | 8H | 3G | 9H | 0 | 0 | 0 | 0 | 0 | 1C | 3C,9G |
| Cocklebur | 8H | 8H | 8H | 8H | 0 | 9H | — | 9H | 3H | 9H | 0 | 0 | 2G | — | — | 6H | 9H |
| Sicklepod | 9G | 9G | 5G | 7G | 0 | 7G | 2G | 1C | 2C | 1C | 0 | 0 | — | 0 | — | 1C,5G | 2C,5G |
| Crabgrass | 3G | 10E | 0 | 5G | 0 | 0 | 0 | 0 | 2C,8G | 2C,5G | 0 | 0 | 0 | 0 | 0 | 0 | 2C,8G |
| Barnyardgrass | 3C,7G | 5G | 1C | 2C | 0 | 3G | 3H | 2G | 4C,8G | 5C,9H | 0 | 0 | 2G | 0 | 0 | 1C | 3G |
| Wild Oats | 3C,7G | 3C,6G | 2C | 2C | 0 | 3G | 5C,9G | 5C,9G | 0 | 0 | 0 | 0 | 0 | 0 | 2C | 0 | 2C |
| Wheat | 3C,8H | 6G | 0 | 0 | 0 | 2G | 1C | 1C | 0 | 0 | 0 | 0 | 2C | 0 | 2G | 0 | 3C,8H |
| Corn | 4U,9G | 2C,9G | 3H | 1H | 2C,2H | 2C,6H | 2C,5H | 2C,9G | 2C,5H | 2C,9G | 0 | 2H | 3U,9G | 0 | 8G | 0 | 3C,9G |
| Soybean | 8H | 1H | 1C | 2C | 2C | 2C | 1C,1H | 3C,5H | 1C | 3C,6H | 0 | 0 | 2C,3G | 0 | 2C,4G | 2C | 3C,9H |
| Rice | 9H | 9H | 2G | 2G | 2C,5G | 9H | 2C,7G | 10E | 2C,6G | 4C,9H | 0 | 0 | 4C,9H | 0 | 2C,9H | 2C | 4C,9H |
| Sorghum | 3C,9H | 2C,9G | 0 | 2G | 0 | 4C,9G | 3C,9H | 3C,9H | 2G | 3C,7H | — | 0 | 3C,6G | 0 | 3C,7G | 2C | 4C,9H |
| Sugar beet | — | — | — | — | 4C,9G | — | — | — | — | — | — | — | 0 | — | 0 | 1C,2G | 9C |
| Cotton | — | — | — | — | — | 6G | — | — | — | — | — | — | — | — | — | — | 9C |

| | Cmpd. 11 | Cmpd. 12 | Cmpd. 13 | Compound 14 | | Cmpd. 15 | Cmpd. 16 | Cmpd. 17 | Cmpd. 18 |
|---|---|---|---|---|---|---|---|---|---|
| Rate kg/ha | 0.05 | 0.05 | 0.05 | 0.05 | 0.4 | 0.05 | 0.05 | 0.05 | 0.05 |
| | POST-EMERGENCE | | | | | | | | |
| Bush bean | 5C,9G,6Y | 4C,9G,6Y | 4C,9G,6Y | 5C,8G,6Y | — | 3S,8G,6Y | 9C | 5C,9G,6Y | 3C,9G,6Y |
| Cotton | 4C,8G | 4C,9H | 2C,4G | 2C | 3C,5G | 2C,3G | 3C,9G | 4C,8G | 4C,8G |
| Morningglory | 4C,8G | 4C,9H | 2C,4H | 2C | 3C,5G | 2C | 5C,9G | 3C | 3C,7H |
| Cocklebur | 9C | 10C | 2C | 2C | 3C,8H | 2C | 4C,9G | 5C,9G | 2C,8G |
| Sicklepod | 3C,6H | 5C,9H | 2C | 0 | 3C,5H | 1C | 6C,9G | 6C,9G | 3C,5G |
| Nutsedge | 2C,7G | 3C,8G | 4G | 0 | 1C,4G | 0 | 4C,9H | 9G | 9G |
| Crabgrass | 1C | 4G | 0 | 1C,2H | 1C,3G | 3C,6H | 4C,9H | 4C,8G | 3C,3G |
| Barnyardgrass | 2C,7H | 9C | 1C | 0 | 2C,6H | 3C,6G | 3C,9G | 2C,7G | 1C |
| Wild Oats | 1C,4G | 5G | 3G | 1C | 4G | 0 | 5C,9G | 5U,9C | 2G |
| Wheat | 8G,5X | 7G | 3G | 0 | 3G | 1C,3G | 2C,9G | 9C | 9G,5I |
| Corn | 2C,9H | 2U,9G | 2C,8H | 1C | 1U,8G | 2C,3G | 5C,9G | 9C | 3C,9G |
| Soybean | 5C,9G | 9C | 2C,4G | 1C,2H | 6C,9H | 4C,8G | 5C,9G | 4C,9G | 5C,9G |
| Rice | 4C,9H | 2C,9G | 5C,9G | 5C,9G | 5C,9G | 4C,9G | 5C,9G | 3C,9G | 9G,5I |
| Sorghum | 3C,8H | 10C | 3C,7H | 1C,5G | 3C,9H | — | — | — | — |
| Sugar beet | | | | 2C,5G | 3C,8H | | | | |

TABLE A-continued

| | | | | PRE-EMERGENCE | | | | | |
|---|---|---|---|---|---|---|---|---|---|
| Morningglory | 9G | 9C | 1C,2H | 2C | 9G | 2G | 9G | 9G | 2C,7H |
| Cocklebur | 9H | 9H | 5G | 0 | 8G | 0 | 8H | 8H | 2G |
| Sicklepod | 9G,2C | 9G | 1C | 1C | 8G | 1H | 9G | 9G | 4G |
| Nutsedge | 7G | 8G | 0 | 0 | 0 | 0 | 6G | 10E | 0 |
| Crabgrass | 0 | 1C | 0 | 0 | 0 | 0 | 2C,8G | 3C,6G | 3G |
| Barnyardgrass | 2C,6G | 3C,8H | 1C | 0 | 2C | 1C | 6C,9H | 3C,9H | 2C |
| Wild Oats | 3G | 2C,7G | 2C | 1C | 2C,8G | 1H | 4C,7G | 2C,6H | 4G |
| Wheat | 2C,9H | 2C,9G | 3C,8G | 1H | 2C,8G | 0 | 2C,9G | 9G | 1C,6G |
| Corn | 2C,9H | 2C,6H | 2C,6G | 6H | 3C,8H | 2C,3G | 3C,9H | 4C,9G | 2C,7G |
| Soybean | 2C,5H | 2C,9H | 1C | 2C,6G | 2C,2H | 1C,1H | 3C,9H | 5H | 2C,2H |
| Rice | 3C,8H | 3C,9H | 2C,9H | 0 | 10E | 0 | 3C,9H | 9H | 9H |
| Sorghum | 3C,9H | 10E | 4C,9H | — | 4C,9H | 3C,4G | 9H | 5C,9H | 2C,9G |
| Sugar beet | 10E | — | 1C,1H | — | 4C,8G | — | — | — | — |
| Cotton | — | — | — | — | 6G | — | — | — | — |

Several compounds were tested according to the procedure described below to further define their activity as pre-emergence herbicides.

TEST B

Two plastic bulb pans were filled with fertilized and limed Woodstown sandy loam. One pan was planted with corn, sorghum, Kentucky bluegrass and several grass weeds. The other pan was planted with cotton, soybeans, purple nutsedge (*Cyperus rotundus*), and several broadleaf weeds. The following grass and broadleaf weeds were planted: crabgrass (*Digitaria sanguinalis*), barnyardgrass (*Echinochloa crusgalli*), wild oats (*Avena fatua*), johnsongrass (*Sorghum halepense*), dallisgrass (*Paspalum dilatatum*), giant foxtail (*Setaria faberii*), cheatgrass (*Bromus secalinus*), mustard (*Brassica arvensis*), cocklebur (*Xanthium pensylvanicum*), morningglory (*Ipomoea hederacea*), sicklepod (*Cassia obtusifolia*), teaweed (*Sida spinosa*), velvetleaf (*Abutilon theophrasti*), and jimsonweed (*Datura stramonium*). A 12.5 cm diameter plastic pot was also filled with prepared soil and planted with rice and wheat. Another 12.5 cm pot was planted with sugar beets. The above four containers were treated pre-emergence with several test compounds within the scope of the invention.

Twenty-eight days after treatment, the plants were evaluated and visually rated for response to the chemical treatments utilizing the rating system described previously for Test A. The data for several compounds are summarized in Table B. A number of other compounds were also tested and all were shown to have activity as pre-emergence treatments for the control of a number of species at rates as low as 0.03 kg/ha. Several of the compounds were safe on wheat.

TABLE B
PRE-EMERGENCE ON WOODSTOWN SANDY LOAM

| | Compound 1 | | Compound 2 | |
|---|---|---|---|---|
| Rate kg/ha | 0.03 | 0.12 | 0.03 | 0.12 |
| Crabgrass | 0 | 0 | 4G | 5G |
| Barnyardgrass | 0 | 4G | 2G | 5G,3H |
| Sorghum | 8G,5H | 9G,9C | 7G,5H | 9G,9C |
| Wild Oats | 3G | 6G | 0 | 5G |
| Johnsongrass | 4G | 4G | 0 | 4G,3H |
| Dallisgrass | 6G | 9G | 3G | 3G |
| Giant foxtail | 2G | 2G | 0 | 0 |
| Ky. bluegrass | 0 | 8G | 0 | 6G |
| Cheatgrass | 7G | 9G | 6G | 8G |
| Sugar beets | 7G | 8G | 5G | 7G |
| Corn | 3G,3C | 6G,3C | 2G | 4G,3C |
| Mustard | 9G,9C | 9G,9C | 8G | 9G |
| Cocklebur | 2G | 6G | 0 | 6G |
| Nutsedge | 10C | 10C | 5G | 10C |
| Cotton | 4G | 6G | 4G | 6G |
| Morningglory | 5G,3C | 6G,3H | 0 | 5G,5H |
| Sicklepod | 7G | 7G | 0 | 7G |
| Teaweed | — | — | — | — |
| Velvetleaf | 10C | 10C | 8G | 9G,9C |
| Jimsonweed | 4G | 8G,8C | 0 | 8G,8C |
| Soybean | 3G,3C | 7G,5C | 2G,2C | 5G,3C |
| Rice | 9G,9C | 10C | 8G | 10C |
| Wheat | 0 | 2G | 0 | 0 |

Several compounds were tested according to the following procedure to better defined their post-emergence utility.

TEST C

The test chemicals, dissolved in a non-phytotoxic solvent, were applied in an overall spray to the foliage and surrounding soil of selected plant species. One day after treatment, plants were observed for rapid burn injury. Approximately fourteen days after treatment, all species were visually compared to untreated controls and rated for response to treatment. The rating system was as described previously for Test A. The data are presented in Table C.

All plants species were seeded in Woodstown sandy loam soil and grown in a greenhouse. The following species were grown in soil contained in plastic pots (25 cm diameter by 13 cm deep): soybeans, cotton, alfalfa, corn, rice, wheat, sorghum, velvetleaf (*Abutilon theophrasti*), sesbania (*Sesbania exaltata*), sicklepod (*Cassia obtusifolia*), morningglory (*Ipomoea hederacea*), jimsonweed (*Datura stramonium*), cocklebur (*Xanthium pensylvanicum*), crabgrass (Digitaria sp.), nutsedge (*Cyperus rotundus*), barnyardgrass (*Echinochloa crusgalli*), giant foxtail (*Setaria faberii*) and wild oats (*Avena fatua*). The following species were grown in soil in a paper cup (12 cm diameter by 13 cm deep): sunflower, sugar beets, and rape. All plants were sprayed approximately 14 days after planting. Additional plant species, such as johnsongrass and field bindweed, are sometimes added to this standard test in order to evaluate unusual selectivity.

Several of the compounds tested by this procedure are useful for the post-emergence control of weeds in wheat.

TABLE C

| Over-the-Top Soil/Foliage Treatment | | | |
|---|---|---|---|
| Rate kg/ha | 0.06 | 0.015 | 0.004 |
| | Compound 1 | | |
| Soybeans | 9C | 6C,8G | 3C,4G |
| Velvetleaf | 9C | 9G | 8G |
| Sesbania | 9G | 6C,7G | 3G |
| Sicklepod | 8G | 7G | 3G |
| Cotton | 8G | 7G | 3G |
| Morningglory | 9G | 7G | 3G |
| Alfalfa | 9C | 8C | 4G |
| Jimsonweed | 9G | 6G | 4G |
| Cocklebur | 9G | 5G | 0 |
| Sunflower | 9G | 7C | 4G |
| Rape | 10C | 9C | 5G |
| Sugar beets | 10C | 9C | 8G |
| Corn | 7G,5C | 6G,2C | 3H,4G |
| Crabgrass | 0 | 0 | 0 |
| Rice | 3G,6C | 2G,4C | 1G |
| Nutsedge | 3G | 2C | 0 |
| Barnyardgrass | 3G | 2G | 0 |
| Wheat | 3G | 1G | 0 |
| Giant foxtail | 4G | 1G | 0 |
| Wild Oats | 7G,4C | 2G | 0 |
| Sorghum | 8G | 8G | 7G |
| Johnsongrass | 4C,5G | 3G | 0 |
| Field Bindweed | 8G | 8G | 2G |
| | Compound 2 | | |
| Soybeans | 10C | 7G | 2G |
| Velvetleaf | 10C | 9G | 7G |
| Sesbania | 10C | 8G | 5G |
| Sicklepod | 10C | 9G | 5G |
| Cotton | 9G | 9G | 9G |
| Morningglory | 9G,5C | 8G | 0 |
| Alfalfa | 9G,5C | 9G | 9G |
| Jimsonweed | 4G | 0 | 0 |
| Cocklebur | 8G | — | 3G |
| Sunflower | 10P | 10P | 3G |
| Rape | 10C | 9G,5C | 6G |
| Sugar beets | 10C | 10C | 10C |
| Corn | 8G | 8G,2H | 3G |
| Crabgrass | 8G | 0 | 0 |
| Rice | 7G | 7G | 2G |
| Nutsedge | 8G | 8G | 0 |
| Barnyardgrass | 8G | 5G | 0 |
| Wheat | 2G | 0 | 0 |
| Giant foxtail | 2G | 2G | 2G |
| Wild Oats | 4G | 4G | 0 |
| Sorghum | 7G | 7G | 2G |

TABLE C-continued

| Over-the-Top Soil/Foliage Treatment | | | |
|---|---|---|---|
| Rate kg/ha | 0.06 | 0.015 | 0.004 |
| Johnsongrass | 7G | 7G | 2G |
| Field Bindweed | 8G | 9G | 4G |

The following test was performed to investigate the utility of compounds of this invention as selective herbicides in wheat and barley.

TEST D

Two plastic pans lined with polyethylene liners were filled with prepared Woodstown sandy loam soil. One pan was planted with seeds of wheat (*Triticum aestivum*), barley (*Hordeum vulgare*), wild oats (*Avena fatua*), cheatgrass (*Bromus secalinus*), blackgrass (*Alopecurus myosuroides*), annual bluegrass (*Poa annua*), green foxtail (*Setaria viridis*), Italian ryegrass (*Lolium multiflorum*) and rapeseed (*Brassica napus*). The other pan was planted with seeds of Russian thistle (*Salsola kali*), cleavers (*Galium aparine*), speedwell (*Veronica persica*), kochia (*Kochia scoparia*), shepherd's purse (*Capsella bursa-pastoris*), *Matricaria inodora*, black nightshade (*Solanum nigrum*), wild buckwheat (*Polygonum convolvulus*) and sugar beets (*Beta vulgaris*). Other species which sometimes are added to this test include downy brome (*Bromus tectorum*), quackgrass (*Agropyron repens*), ripgut brome (*Bromus rigidus*), tansy mustard (*Descurainia pinnata*), tumble mustard (*Sisymbrium altissimum*) and yellow rocket (*Barbarea vulgaris*). The above two pans were treated pre-emergence. At the same time two pans in which the above plant species were already growing were treated post-emergence. Plant height at the time of treatment ranged from 1–20 cm depending on plant species.

The compounds applied were diluted with a non-phytotoxic solvent and sprayed over-the-top of the pans. An untreated control and a solvent alone control were included for comparasion. All treatments were maintained in the greenhouse for 19–22 days at which time the treatments were compared to the controls and the effects visually rated. The recorded data for one of the compounds are presented in Table D. It can be seen that Compound No. 2 has utility for pre - or post-emergence weed control in wheat and barley.

TABLE D

| Rate g/ha | 4 | 15 | 60 |
|---|---|---|---|
| | Compound 2 | | |
| | Pre-Emergence | | |
| wheat | 0 | 0 | 1G |
| barley | 0 | 0 | 0 |
| wild oats | 0 | 0 | 6G |
| downy brome | 0 | 2G | 9G |
| cheatgrass | 0 | 2G | 5G |
| blackgrass | 0 | 0 | 6G |
| annual bluegrass | 0 | 0 | 5G |
| green foxtail | 0 | 0 | 3G |
| quackgrass | 0 | 3G | 6G |
| Italian ryegrass | 0 | 2C,5G | 7C,9G |
| ripgut brome | 0 | 4G | 8G |
| Russian thistle | 0 | 0 | 0 |
| tansy mustard | 2C,9G | 10C | 10C |
| Galium aparine | — | — | — |
| tumble mustard | 8G | 2C,8G | 10C |
| kochia | 0 | 0 | 8G |
| shepherd's purse | 2C,8G | 10C | 9C,9G |
| *Matricaria inodora* | 8G | 9G | 8C,9G |
| black nightshade | 0 | 2G | 5G |
| yellow rocket | 2G | 2C,6G | 9G |
| rapeseed | 2G | 2C,8G | 2C,9G |
| wild buckwheat | 0 | 2G | 4G |
| | Post-Emergence | | |
| wheat | 0 | 0 | 2G |
| barley | 0 | 0 | 2G |
| wild oats | 0 | 0 | 3G |
| downy brome | 0 | 2G | 4G |
| cheatgrass | 0 | 2G | 3G |
| blackgrass | 0 | 3G | 5G |
| annual bluegrass | 3G | 4G | 5G |
| green foxtail | 0 | — | — |
| quackgrass | 0 | 0 | 6G |
| Italian ryegrass | 0 | 6G | 1C,6G |
| ripgut brome | 0 | 0 | 5G |
| Russian thistle | 0 | — | 0 |
| tansy mustard | 7G | 3C,8G | 9C,9G |
| *Galium aparine* | 3C,8G | 8G | 10C |
| tumble mustard | 10C | 9C,9G | 10C |
| kochia | 3G | 5G | 8G |
| shepherd's purse | 6G | 7C,8G | 10C |
| *Matricaria inodora* | 6G | 3C,8G | 9C,9G |
| black nightshade | 5G | 4G | 4G |
| yellow rocket | 5G | 7G | 7C,8G |
| rapeseed | 7G | 8G | 5C,8G |
| wild buckwheat | 5G | 8G | 3C,8G |

What is claimed is:

1. A compound of the formula:

QSO₂NHCONHA where
Q is

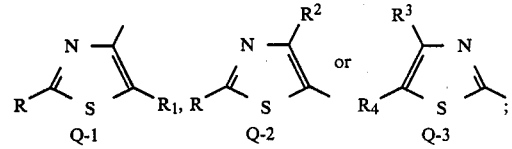

R is H, C₁–C₃ alkyl or CH₃C(O)NH;
R₁ is H, C₁–C₃ alkyl, C₁–C₃ alkoxy, C₁–C₃ alkylthio, or C₁–C₃ alkoxycarbonyl;
R₂ is H, C₁–C₃ alkyl, C₁–C₃ alkoxy, C₁–C₃ alkylthio, C₁–C₃ alkoxycarbonyl, NO₂, Cl, Br or CF₃;
R₃ is H, Cl or CH₃;
R₄ is H, Cl or CH₃;
A is

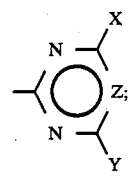

X is CH₃, OCH₃, OCF₂H, OC₂H₅ or CH₂OCH₃;
Y is CH₃, OCH₃, or OCF₂H; and
Z is CH or;

provided that (i) R₃ and R₄ are not simultaneously Cl, and (ii) when either X or Y is OCF₂H, then Z is CH; and agriculturally suitable salts thereof.

2. A compound of claim 1 where Q is

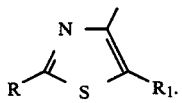

3. A compound of claim 1 where Q is

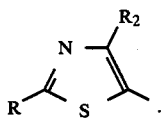

4. A compound of claim 1 where Z is CH.

5. A compound of claim 2 where Z is CH.

6. A compound of claim 3 where Z is CH.

7. A compound of claim 2 where Z is CH, R is H or CH$_3$, and R$_1$ is H, CH$_3$, C$_1$-C$_2$ alkoxy or C$_1$-C$_2$ alkoxycarbonyl.

8. The compound of claim 1 which is N-[(4-methoxy-6-methylpyrimidin-2-yl)aminocarbonyl]-4-thiazolesulfonamide.

9. The compound of claim 1 which is N-[(4,6-dimethoxypyrimidin-2-yl)aminocarbonyl]-4-thiazolesulfonamide.

10. The compound of claim 1 which is 5-ethoxy-N-[(4,6-dimethoxypyrimidin-2-yl)aminocarbonyl]-2-methyl-4-thiazolesulfonamide.

11. An agricultural composition comprising an herbicidally effective amount of one or more compounds of any one of claims 1–10 and at least one of the following: (a) a surfactant and (b) a solid or liquid diluent.

12. A method for controlling the growth of undesired vegetation comprising applying to the locus of such vegetation an agriculturally effective amount of one or more compounds of any one of claim 1–10.

* * * * *